US006893411B1

United States Patent
Modglin

(10) Patent No.: US 6,893,411 B1
(45) Date of Patent: May 17, 2005

(54) THIGH CUFF EXTENSION

(75) Inventor: Michael D. Modglin, Braselton, GA (US)

(73) Assignee: DeRoyal Industries, Inc., Powell, TN (US)

( * ) Notice: Subject to any disclaimer, the term of this patent is extended or adjusted under 35 U.S.C. 154(b) by 37 days.

(21) Appl. No.: 10/395,762

(22) Filed: Mar. 21, 2003

(51) Int. Cl.$^7$ .................................................. A61F 5/00
(52) U.S. Cl. ............................ 602/23; 602/12; 602/14; 128/882
(58) Field of Search .............................. 602/5, 12, 16, 602/19, 23, 24, 25, 60, 62; 128/882, 873, 875, 876, 100.1; 2/22, 33, 404, 227, 228, 231, 232, 233, 239–242, 255, 256

(56) References Cited

U.S. PATENT DOCUMENTS

| | | | |
|---|---|---|---|
| 1,490,265 A | | 4/1924 | Glasgow |
| 2,332,119 A | * | 10/1943 | Springer .................... 602/19 |
| 2,778,358 A | | 1/1957 | Keles |
| 3,970,079 A | * | 7/1976 | Gaylord, Jr. ............... 602/19 |
| 4,081,150 A | * | 3/1978 | Tyson ....................... 607/112 |
| 4,180,261 A | * | 12/1979 | Kolka ....................... 482/105 |
| 4,556,055 A | * | 12/1985 | Bonner, Jr. ................ 604/304 |
| 4,574,790 A | | 3/1986 | Wellershaus |
| 4,905,678 A | | 3/1990 | Cumins et al. |
| 4,953,543 A | * | 9/1990 | Grim et al. ................. 602/16 |
| 4,957,103 A | | 9/1990 | Young et al. |
| 4,982,732 A | * | 1/1991 | Morris ....................... 602/16 |
| 5,038,760 A | | 8/1991 | Osborn |
| 5,054,476 A | | 10/1991 | Petrofsky et al. |
| 5,133,341 A | * | 7/1992 | Singer et al. ............... 602/16 |
| 5,135,469 A | * | 8/1992 | Castillo ...................... 602/16 |
| 5,344,391 A | | 9/1994 | Modglin |
| 5,533,961 A | * | 7/1996 | Iwata ......................... 602/19 |
| 5,618,264 A | * | 4/1997 | Vasquez ..................... 602/24 |
| 5,620,412 A | | 4/1997 | Modglin |
| 5,814,001 A | * | 9/1998 | Schwenn et al. ........... 602/24 |
| 5,814,002 A | * | 9/1998 | Nelson ....................... 602/27 |
| 5,816,251 A | | 10/1998 | Glisan |
| 5,823,984 A | * | 10/1998 | Silverberg .................. 602/61 |
| 5,967,998 A | | 10/1999 | Modglin |
| 5,983,391 A | * | 11/1999 | Palmer et al. ................ 2/16 |
| 6,039,677 A | * | 3/2000 | Spletzer ..................... 482/105 |
| 6,066,108 A | | 5/2000 | Lundberg |
| 6,105,163 A | * | 8/2000 | Edmiston ..................... 2/22 |
| 6,190,342 B1 | | 2/2001 | Taylor |
| 6,503,217 B1 | * | 1/2003 | Gibbs et al. ................ 602/23 |
| 6,589,195 B1 | * | 7/2003 | Schwenn et al. ........... 602/23 |
| 6,671,887 B1 | * | 1/2004 | Eligan et al. ................ 2/228 |
| 2003/0135146 A1 | * | 7/2003 | Daneshvar .................. 602/60 |

FOREIGN PATENT DOCUMENTS

EP        0581041 A2 *  2/1994  ............ A61F/5/00

* cited by examiner

Primary Examiner—Henry Bennett
Assistant Examiner—Amanda Wieker
(74) Attorney, Agent, or Firm—Luedeka Neely & Graham PC

(57) ABSTRACT

A thigh cuff extension for use with a medical brace. The thigh cuff extension includes a plurality of flexible and conformable body portions releasably and adjustably connectable to one another so as to provide a cuff body adjustably positionable to snugly encircle the thigh of a user, at least one substantially rigid stay member associated with each of the body portions, and an extension member associated with one of the rigid stay members and connectable to the medical brace.

9 Claims, 6 Drawing Sheets

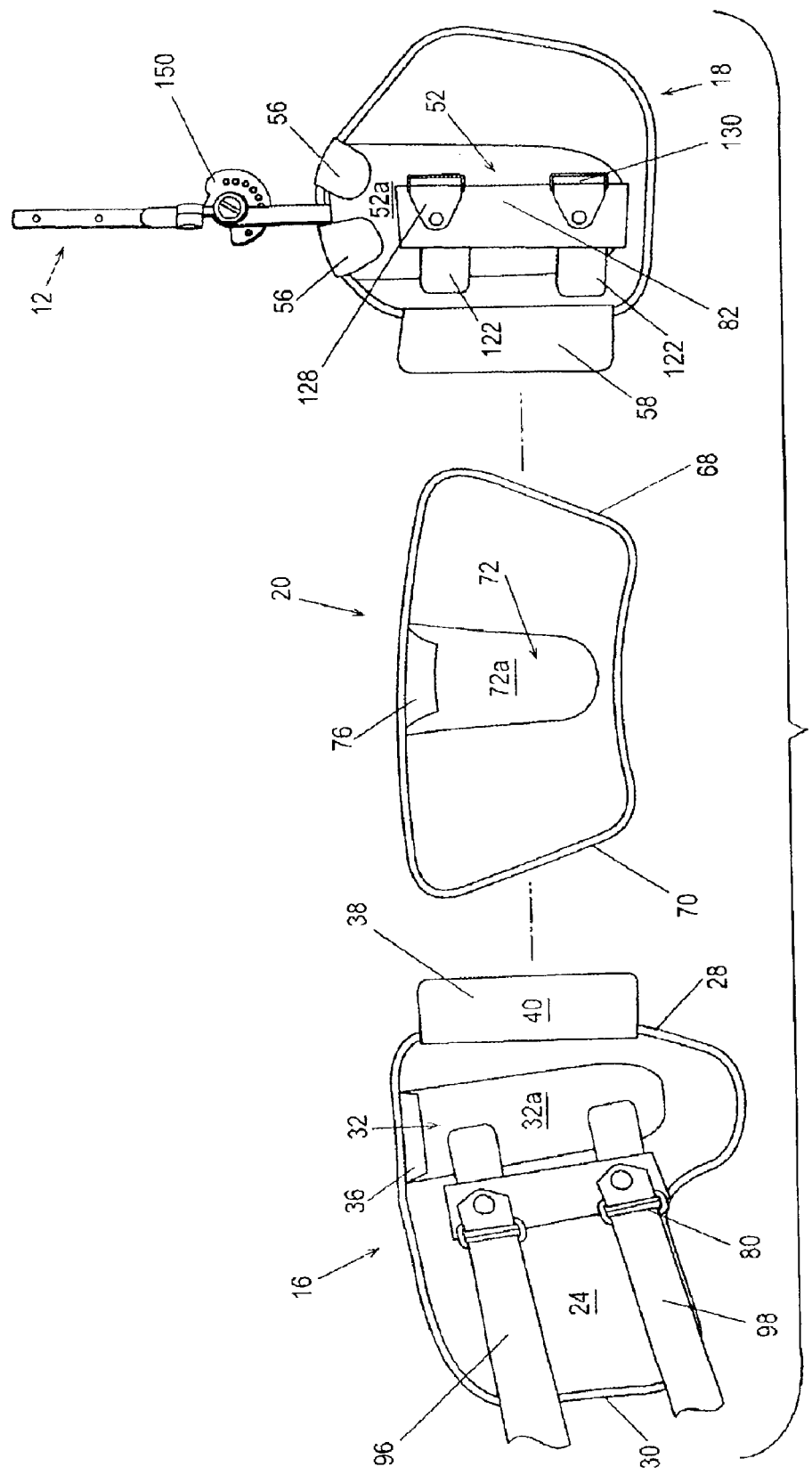

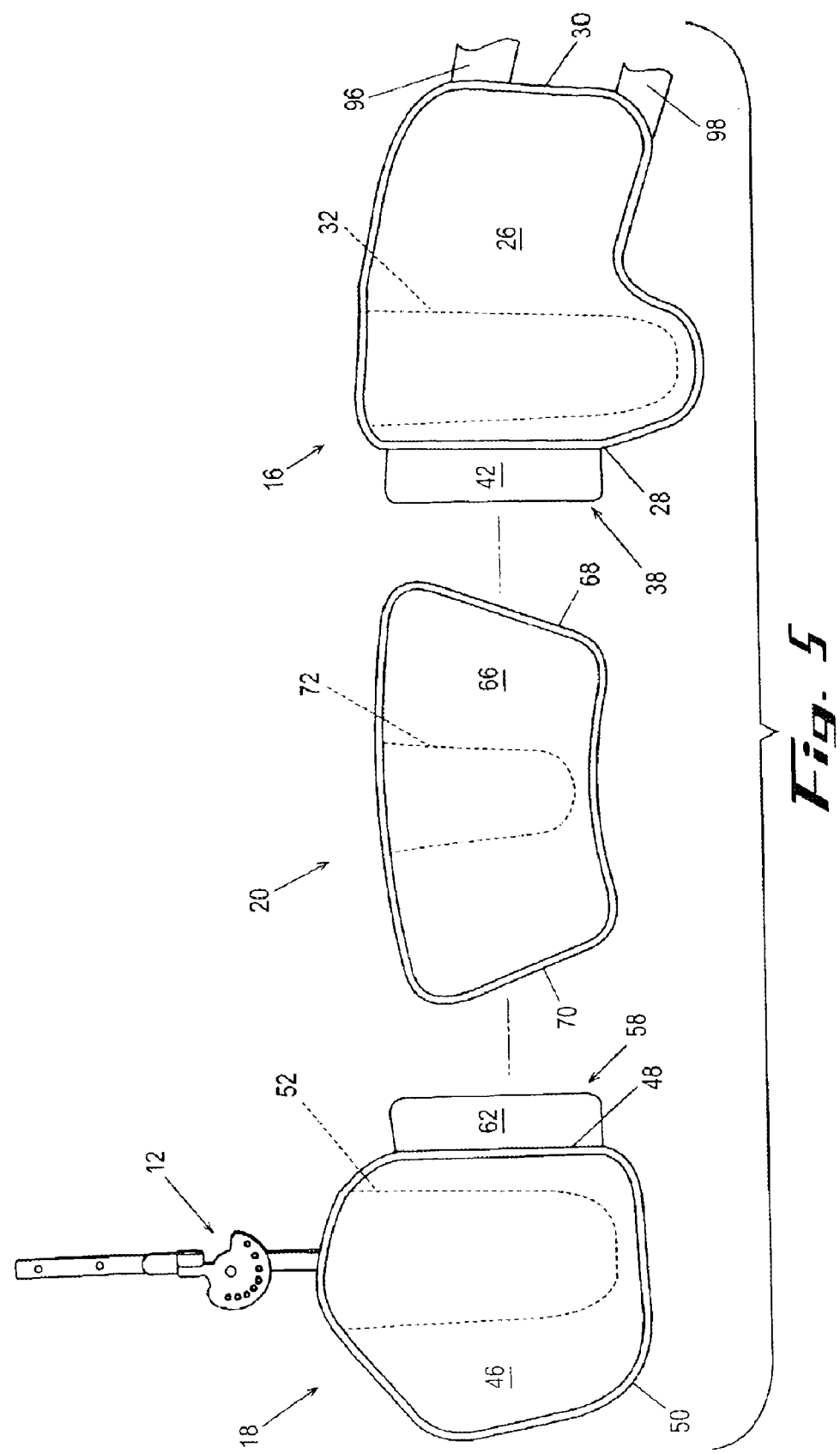

THIGH CUFF EXTENSION

FIELD OF THE INVENTION

This invention relates generally to medical orthoses. More particularly, this invention relates to thigh cuff extension devices for use with medical braces.

BACKGROUND AND SUMMARY OF THE INVENTION

Thigh cuff extension devices are commonly used in conjunction with back braces, hip braces, and the like. Conventional thigh cuff extensions desire improvement, particularly in terms of comfort and adjustability.

In a preferred embodiment, the invention relates to an improved thigh cuff extension for use with a medical brace. The thigh cuff extension includes a plurality of flexible and conformable body portions releasably and adjustably connectable to one another so as to provide a cuff body adjustably positionable to snugly encircle the thigh of a user, at least one substantially rigid stay member associated with each of the body portions, and an extension member associated with one of the rigid stay members and connectable to the medical brace.

The cuff offers improved comfort and adjustability. The cuff body is conformable to the contour of the thigh and is easily and conveniently adjusted to fit a variety of thigh sizes. Also, the relative positions of the individual body portions may be adjusted to enable a substantially custom, fit of the cuff to an individual user while still enabling the same cuff structure to be adaptable to a variety of users.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

FIG. 3 is a front plan view of the thigh cuff extension of FIG. 1, with the extension opened to a planar orientation.

FIG. 4 is a partially exploded frontal view of the thigh cuff extension of FIG. 1.

FIG. 5 is a partially exploded rear view of the thigh cuff extension of FIG. 1.

DETAILED DESCRIPTION

Figure 1:
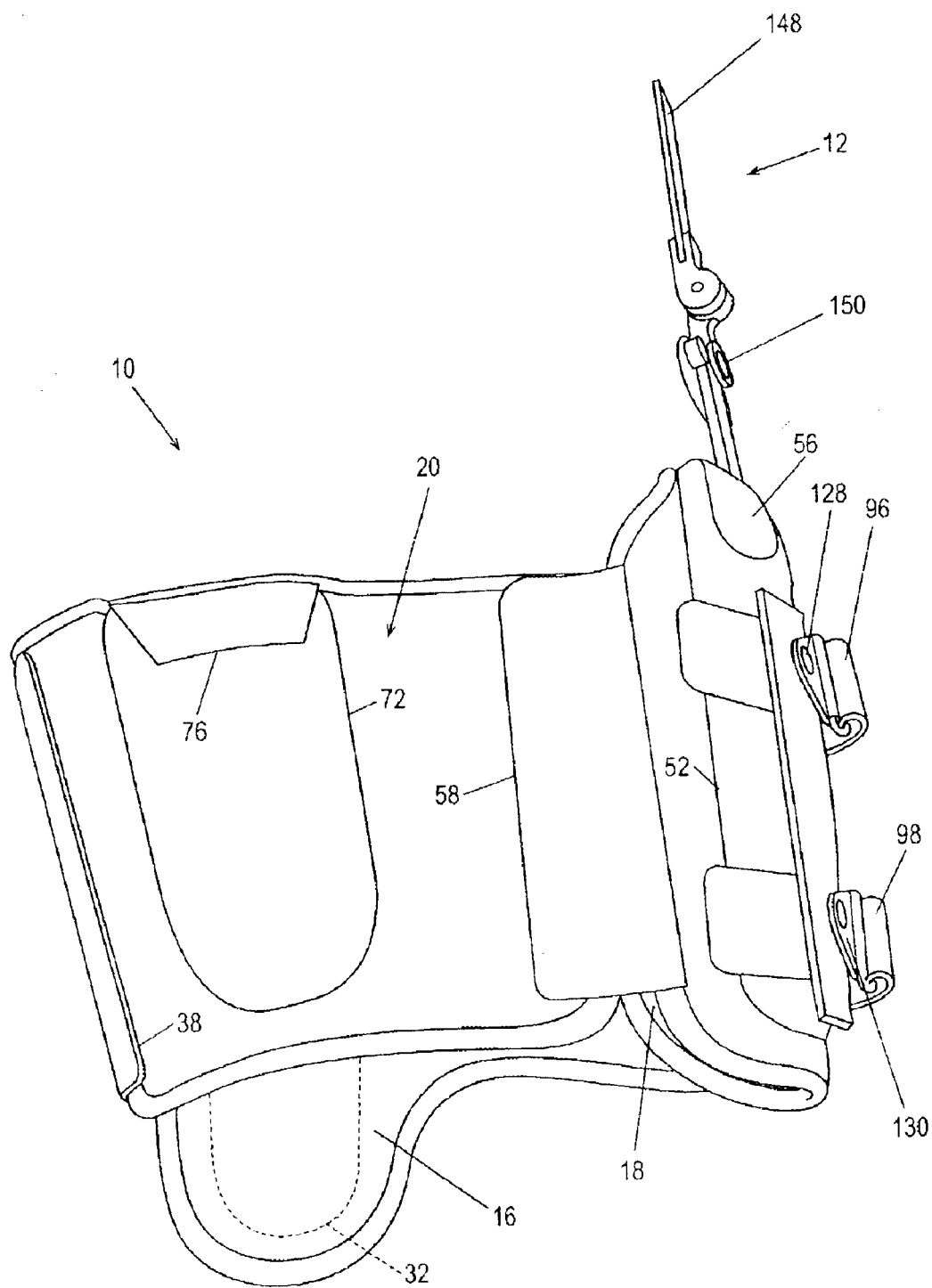
FIG. 1 is a perspective view of a thigh cuff extension in accordance with a preferred embodiment.
Figure 2:
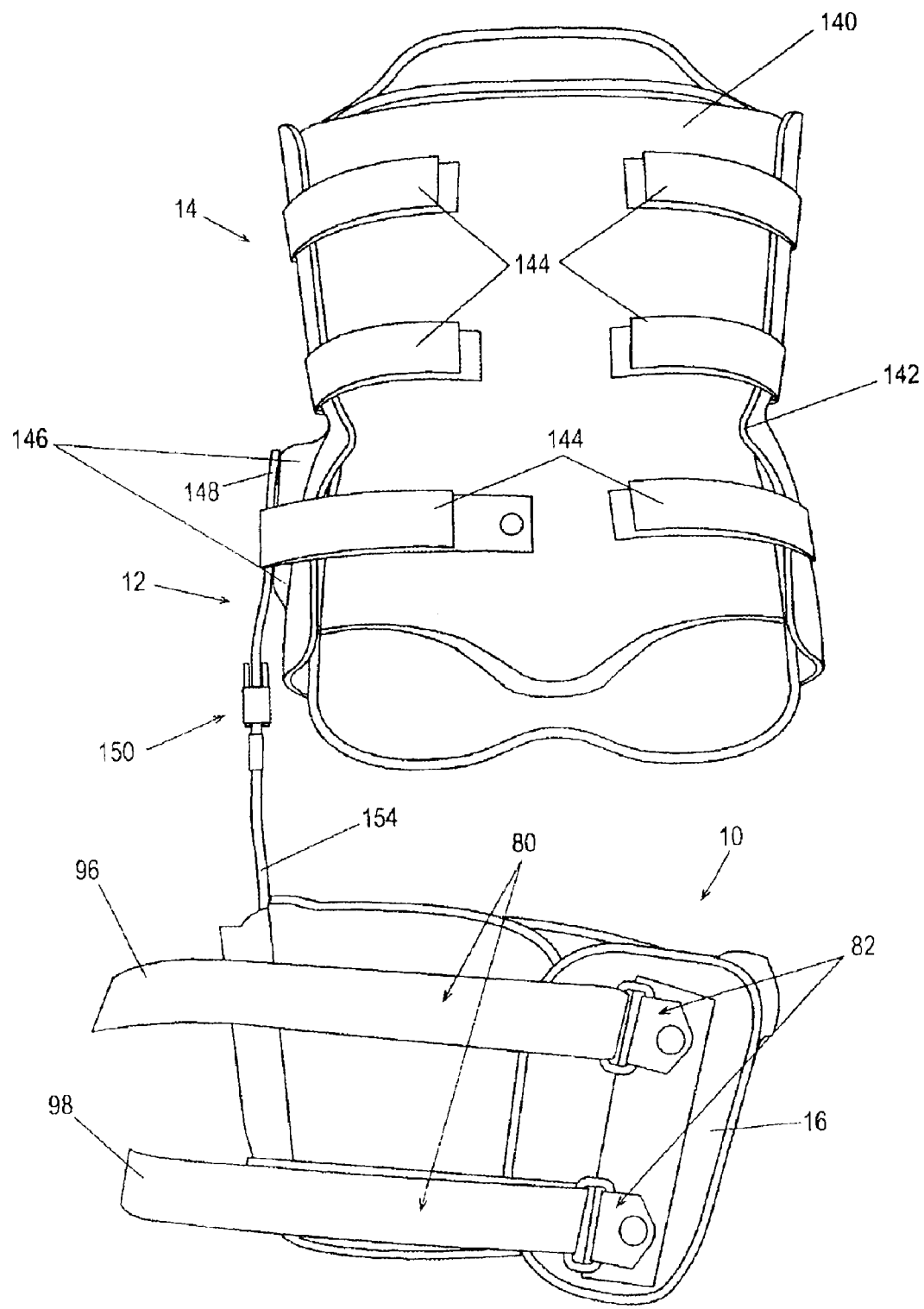
FIG. 2 is a frontal view showing the thigh cuff extension of FIG. 1 attached to a spinal brace.
Figure 1:
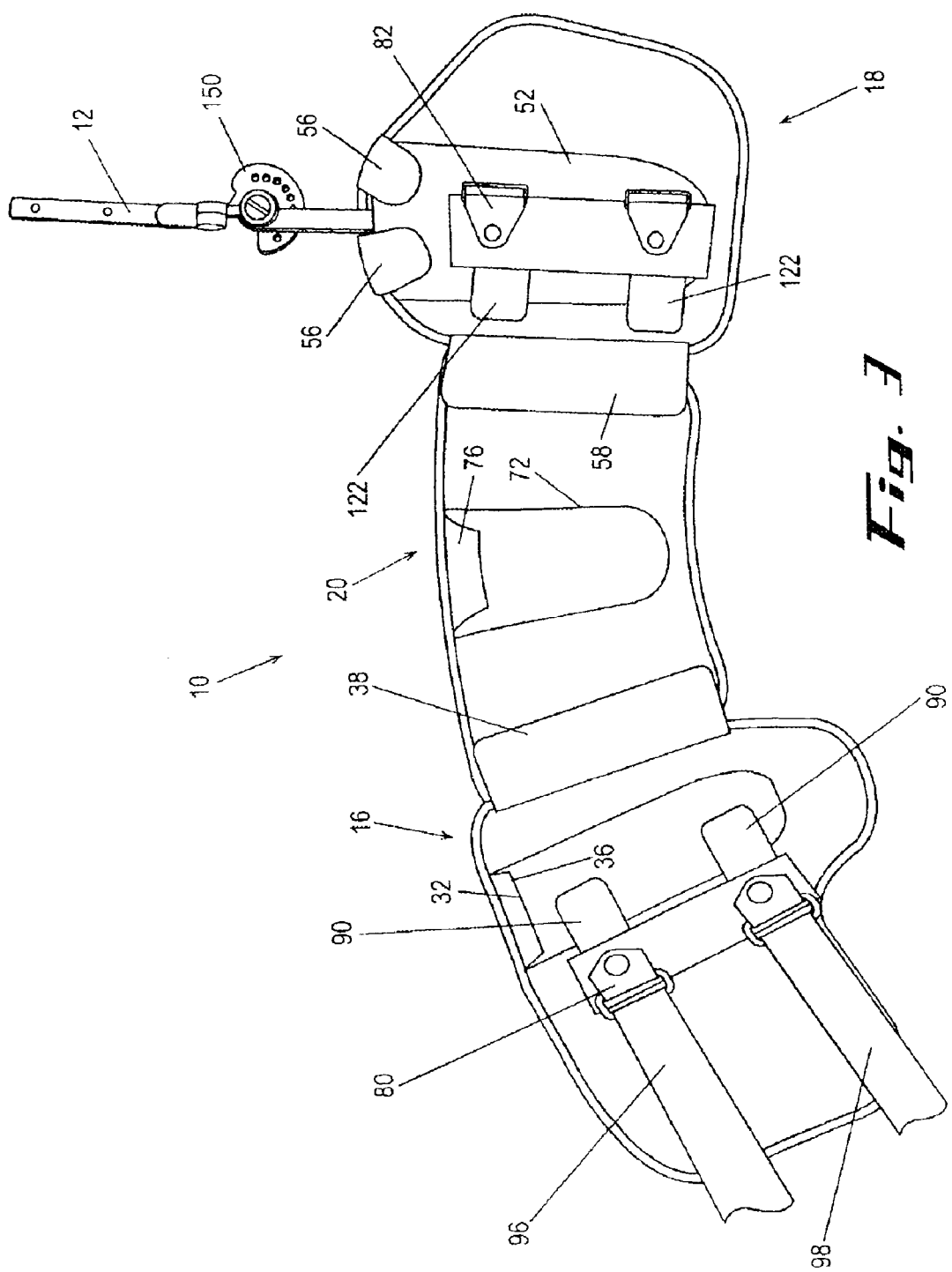
Figure 6:
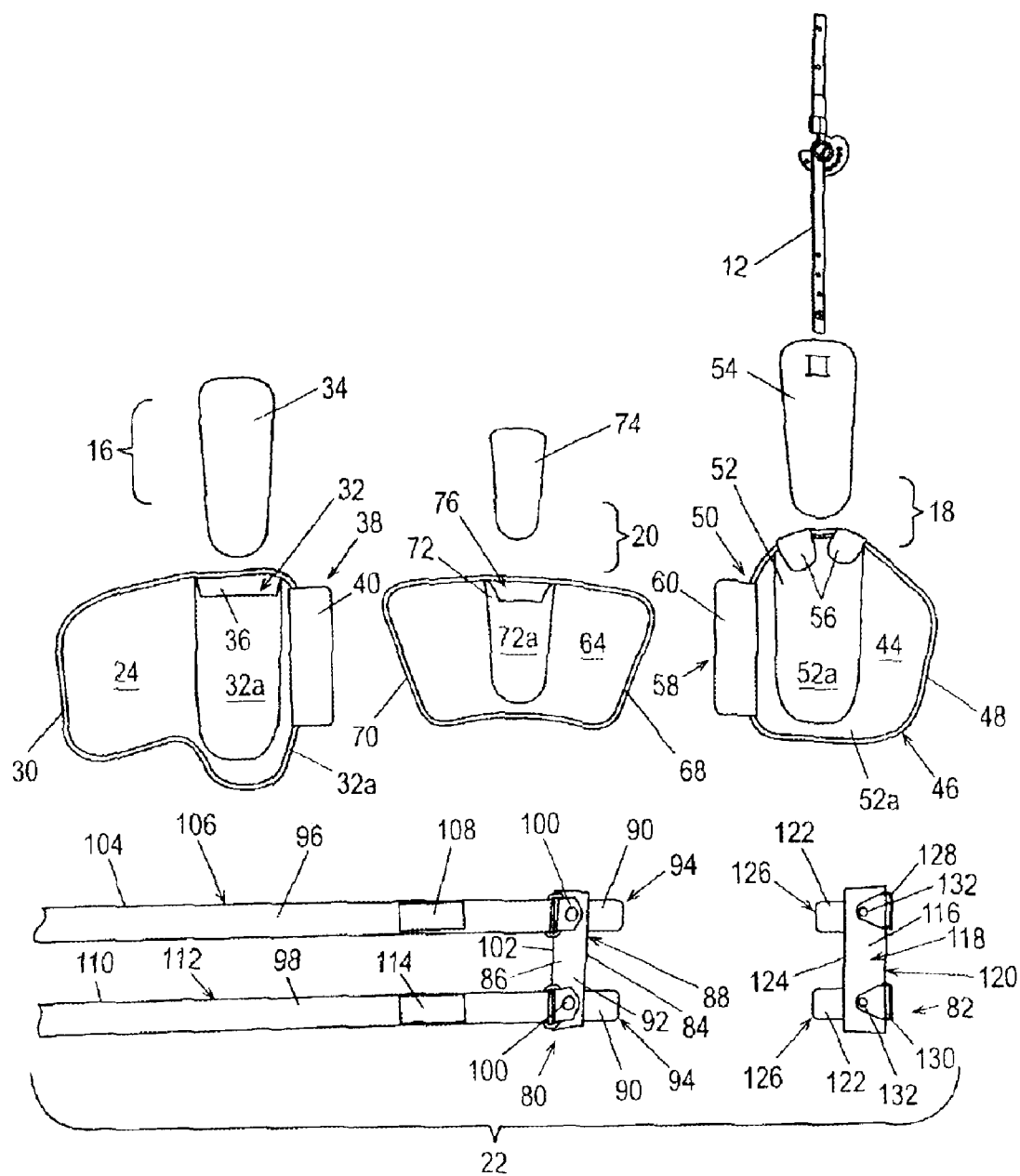
FIG. 6 is a fully exploded frontal view of the components of the thigh cuff extension of FIG. 1.

With initial reference to FIGS. 1 and 2, the invention relates to a thigh cuff 10 connectable, as by an extension member, such as caliper 12, to an orthoses or other medical brace such as spinal brace 14.

With additional reference to FIGS. 3–6, the thigh cuff 10 includes, as major components, a plurality off flexible and conformable body portions releasably and adjustably connectable to one another so as to provide a cuff body positionable to encircle the thigh of a user. For example, in a preferred embodiment, the cuff 10 includes as body portions a first end segment 16, a second end segment 18, and an intermediate segment 20. In addition, the cuff 10 also preferably includes a securement system 22 (FIG. 6) for urging the body portions snugly against the thigh of the user.

The cuff 10 is configured to be worn about the thigh of a user. Accordingly, as the terms "exterior" or "front" are used herein to identify surfaces, such terms are used in the context that an exterior or front surface faces away from the thigh of the user when the cuff is installed thereon. Likewise, the terms "interior" or "rear" are used to reference surfaces that generally face the thigh of the user.

End Segment 16

The first end segment 16 is preferably made of a soft, conformable fabric material, such as an open cell foam laminate. The first end segment 16 has a front or exterior surface 24 opposite a rear or interior surface 26, and opposite ends 28 and 30. The front surface 24 is preferably of suitable material/texture such as a loop material so as to matingly and releasably engage with a hook material, e.g. such as materials available under the tradename VELCRO.

An elongate pocket 32 is preferably located on the front surface 24 of the segment 16 for receiving a rigid elongate stay 34. The stay 34 is preferably a length of a rigid plastic material having a curved cross-section so as to substantially conform to the thigh of a user. Exterior surface 32a of the pocket 32 is preferably made of a loop material of a type suitable for releasably engaging hook material. The pocket 32 preferably includes a closure flap 36. Alternatively, it will be understood that a substantially rigid material, such as a substantially rigid plastic material may be sandwiched within the segment 16 to provide rigidity.

For comfort purposes, the width of the segment 16 adjacent the ends 28 and 30 is preferably less than the width of the segment 16 at the location of the pocket 32. A fastening member, such as a strip of fabric material 38 having loop material 40 on one side and hook material 42 on the opposite side, is preferably secured to the end 28 as by stitches.

End Segment 18

The second end segment 118 is preferably made of the same materials as the first end segment 16 and includes a front or exterior surface 44 opposite a rear or interior surface 46, and opposite ends 48 and 50. The front surface 44 is preferably of suitable material/texture so as to matingly engage with a hook material.

An elongate pocket 52 is preferably located on the front surface 44 of the segment 18 for receiving a rigid elongate stay 54 to which the caliper 12 may connect. The stay 54 is preferably a length of a rigid plastic material having a curved cross-section so as to substantially conform to the thigh of a user and indentations, apertures, or the like for facilitating attachment of the caliper 12 thereto. Exterior surface 52a of the pocket 52 is preferably made of a loop material of a type suitable for releasably engaging hook material. The pocket 52 preferably includes a pair of closure flaps 56. A fastening member, such as a strip of fabric material 58 having loop material 60 on one side and hook material 62 on the opposite side, is preferably secured to the end 48 as by stitches. Alternatively, it will be understood that a substantially rigid material such as a substantially rigid plastic material may be sandwiched within the segment 18 to provide rigidity.

Intermediate Segment 20

The intermediate segment 20 is preferably made of the same material as the segments 16 and 18 and has a front or exterior surface 64 opposite a rear or interior surface 66, and opposite ends 68 and 70. The front surface 64 is preferably of suitable material/texture so as to matingly engage with a hook material.

An elongate pocket 72 is preferably located on the front surface 64 of the segment 20 for receiving a rigid elongate stay 74. The stay 74 is preferably a length of a rigid plastic material having a curved cross-section so as to substantially conform to the thigh of a user. Exterior surface 72a of the pocket 72 is preferably made of a loop material of a type suitable for releasably engaging hook material. The pocket 72 preferably includes a closure flap 76. Alternatively, it will be understood that a substantially rigid material, such as a substantially rigid plastic material may be sandwiched within the segment 20 to provide rigidity.

Securement System 22

The securement system 22 includes a strap assembly 80 and a buckle assembly 82. The strap assembly 80 includes a fastening member, such as a strip of fabric material 84 having an exterior or front surface 86 and opposite rear or interior surface 88. The interior surface 88 is preferably provided by a hook material secured to the fabric material 84 as by adhesive or stitches. A pair of securement tabs 90 preferably extend outwardly from an edge 92 of the fabric material 84. An interior surface 94 of the tabs 90 preferably includes a hook material.

A pair of straps 96 and 98 are secured adjacent the front surface 86 of the material 84 as by fasteners 100. The straps 96 and 98 extend generally perpendicular to the length of the material 84 and away from edge 102 of the material 84. The strap 96 includes a front or exterior surface 104 and an opposite interior or rear surface 106. A strip of hook material 108 is secured, adjacent a portion of the front surface 104 as by stitches. Likewise, the strap 98 includes a front or exterior surface 110 and an opposite interior or rear surface 112. A strip of hook material 114 is secured adjacent a portion of the front surface 110 as by stitches.

The buckle assembly 82 includes a fastening member, such as a strip of fabric material 116 having an exterior or, front surface 118 and opposite rear or interior surface 120. The interior surface 120 is preferably provided by a hook material secured to the fabric material 116 as by adhesive or stitches. A pair of securement tabs 122 preferably extend outwardly from an edge 124 of the fabric material 116. An interior surface 126 of the tabs 122 preferably includes a hook material. A pair of buckles 128 and 130 are secured adjacent the front surface 18 of the material 116 as by fasteners 132.

Assembly and Use

With reference to FIGS. 3–6, the cuff 10 is preferably assembled by assembling the segments 16–20, and then attaching the segments to one another. For example, the end segment 16 may be assembled as by positioning the stay 34 within the pocket 32 and securing the closure flap 36. The strap assembly 80 is then attached to the exterior surface 24 at a desired location by pressing the hook material of the surfaces 94 of the tabs 90 and the hook material of the interior surface 88 of the fabric material 84 against the loop material of the surface 24 and/or of the exterior surface 32a of the pocket 32 and/or the loop material 40 of the fabric material 38.

The strap assembly 80 is preferably oriented such that the length axis of the fabric material 84 is substantially parallel with the length axis of the fabric material 38, as well as the length axis of the stay 34 within the pocket 32. The straps 96 and 98 are oriented so as to align with the length axis of the segment 16 and away from the fabric material 38.

The end segment 18 may be assembled as by positioning the stay 54 within the pocket 52 (with the caliper 12 attached to the stay 54) and securing the closure flaps 56. The buckle assembly 82 is then attached to the exterior surface 44 at a desired location by pressing the hook material of the surfaces 126 of the tabs 122 and the hook material of the interior surface 126 of the fabric material 116 against the loop material of the surface 44 and/or of the exterior surface 52a of the pocket 52 and/or the loop material 60 of the material 58.

The buckle assembly 82 is preferably oriented such that the length axis of the fabric material 116 is substantially parallel with the length axis of the fabric material 58, as well as the length axis of the stay 54 within the pocket 52. The buckles 128 and 130 are oriented away from the fabric material 58.

The intermediate segment 20 may be assembled as by placing the stay 74 within the pocket 72 and closing the flap 72a. The assembled intermediate segment 20 may be attached to the assembled end segments 16 and 18 as by positioning the end segment 16 adjacent the end 70 of the intermediate segment 20 and the end segment 18 adjacent the end 68 of the intermediate segment 20, with the front or exterior surfaces commonly oriented.

The hook material 42 of the fabric material 38 of the end segment 16 is next preferably placed in mating engagement with the loop material of the front surface 64 of the intermediate segment 20, generally at a location adjacent the end 70. Likewise, the hook material 62 of the fabric material 58 of the end segment 18 is placed in mating engagement with the loop material of the front surface 64 of the intermediate segment 20, generally at a location adjacent the end 68. This yields the assembled cuff 10 of FIG. 3. As will be appreciated, the positions of the strap system 80 and the buckle system 82 may be reversed, with the buckle system 82 attached to the end segment 16 and the strap system 80 attached to the end segment 18.

Returning now to FIG. 2, the thus assembled cuff 10 is preferably used in conjunction with an orthoses, such as the brace 14, which is representative of a lumbosacral orthoses. The cuff 10 may also preferably be used with a hip orthosis, knee orthosis, leg orthosis, and the like.

The brace 14 is a conventional bi-valve type orthoses having a pair of rigid shells 140 and 142 and securement straps 144. The shell 142 includes a mount 146 for attachment of an upper end 148 of the caliper 12, as by use of fasteners such as screws, bolts, or the like.

The caliper 12 preferably includes a joint 150 which may be of a variety of well known configurations. For example, the joint may simply be a hinge with free motion, lockable, or with adjustable tension or flexion, such as provided by an adjustable spring. The joint 150 is located intermediate the upper end 148 of the caliper and a lower end 154 of the caliper. Lower end 154 of the caliper is preferably rigidly attached or connected to the stay 54 as by fasteners or mating detents and indentations or the like, the mechanics of which are well known.

As will be appreciated, the orthoses with which the cuff 10 is used, such as the brace 14, is donned by the user and the cuff 10 placed to surround the thigh of the user, with the interior or rear surfaces of the cuff generally facing the thigh of the user. In this regard, it will be appreciated that the cuff 10 is oriented such that the caliper 12 is generally positioned adjacent the outer lateral side of the thigh, with the cuff 10 generally encircling the thigh such that the free needs of the straps 96 and 98 are generally adjacent the buckles 128 and 130. The cuff 10 may then be secured around the thigh by passing the straps 96 and 98 through the buckles 128 and 130, respectively, and folding the straps back toward their fixed ends, with the loop material of the front surfaces 104 and 110 of the straps 96 and 98 secured to the strips of hook material 108 and 114, respectively. As will be appreciated, the rear surface of the end segment 16 and/or the end segment 18 may include a strip of hook material or the like to releasably engage loop material associated with the front surface of the end segment which it overlies when encircling the thigh of the user. That is, if the cuff 10 is encircles about the thigh so that the rear surface of the end segment 16 overlies the front surface of the end segment 18, then hook material may desirably be provided on the rear surface of the end segment 16 to engage the loop material of the front surface of the segment 18.

The construction of the cuff 10 offers significant advantages in terms of comfort and adjustability. For example, each of the segments 16–20 is substantially flexible and conformable to the contour of the thigh and offers enhanced comfort as compared to conventional extension cuffs that are substantially rigid. In addition, the cuff 10 is easily and conveniently adjusted to fit a variety of thigh sizes. That is, the construction of the cuff 10 enables the end segments 16 and 18 to be easily positioned and repositioned relative to one another and to intermediate segment 20 for adjustment of the size of the cuff 10. Also, if need be, the linear relationship between each segment 16 and 18 can be varied relative to the segment 20. Likewise, the position of the strap system 80 and the buckle system 82 can be easily varied relative to the end segments 16 and 18. The modular construction of the cuff coupled with the ability to readily position and re-position the individual components of the cuff 10 relative to one another enables a substantially custom fit of the cuff to an individual user and enables the same cuff structure to be adaptable to a variety of users.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A thigh cuff extension for use with a medical brace, the thigh cuff extension comprising a plurality of flexible and conformable body portions, wherein all of the body portions are releasably and adjustably connectable to one another in an end-to-end relationship about the entire circumference of the thigh of the user so as to provide a continuous cuff body adjustably positionable about the entire circumference of the thigh of a user to snugly encircle and surround the entire circumference of the thigh of the user, at least one substantially rigid stay member associated with each of the body portions, and an extension member rigidly attached to one of the rigid stay members and connectable to the medical brace, wherein the body portions are substantially transversely adjustable about the extension member.

2. The thigh cuff of claim 1, wherein the body portions comprise first and second end segments and an intermediate segment, wherein one end of the first end segment is releasably engageable with a first portion of the intermediate segment and one end of the second end segment is matingly engageable with a second portion of the intermediate segment.

3. The thigh cuff of claim 1, further comprising a securement strap for urging the body portions snugly against the thigh of the user.

4. The thigh cuff of claim 1, wherein each of the body portions includes a pocket for receiving one of the rigid stays.

5. A medical support system, comprising, a medical brace and a thigh cuff extension connected to the medical brace, the thigh cuff extension including a plurality of flexible and conformable body portions, wherein all of the body portions are releasably and adjustably connectable to one another in an end-to-end relationship about the entire circumference of the thigh of a user so as to provide a continuous cuff body adjustably positionable to snugly encircle and surround the entire circumference of the thigh of the user, at least one substantially rigid stay member associated with each of the body portions, and an extension member having a first end connected to one of the rigid stay members and a second end connected to the medical brace, wherein the body portions are substantially transversely adjustable about the extension member.

6. The system of claim 5, wherein the body portions comprise first and second end segments and an intermediate segment, wherein one end of the first end segment is releasably engageable with a first portion of the intermediate segment and one end of the second end segment is matingly engageable with a second portion of the intermediate segment.

7. The system of claim 5, further comprising a securement strap for urging the body portions snugly against the thigh of the user.

8. The system of claim 5, wherein each of the body portions includes a pocket for receiving one of the rigid stays.

9. The system of claim 5, wherein the medical brace comprises a spinal orthosis.

* * * * *